United States Patent
Von Iderstein et al.

[11] Patent Number: 6,105,580
[45] Date of Patent: Aug. 22, 2000

[54] URINE CONTROL DEVICE

[75] Inventors: Irwin F. Von Iderstein, Lady Lake, Fla.; Gordon C. Cheng, Carlisle, Mass.

[73] Assignee: UroScientific, Incorporated, Woburn, Mass.

[21] Appl. No.: 09/030,186

[22] Filed: Feb. 25, 1998

Related U.S. Application Data

[63] Continuation-in-part of application No. 08/979,099, Nov. 26, 1997, which is a continuation of application No. 08/731,246, Oct. 11, 1996, which is a division of application No. 08/333,860, Nov. 3, 1994.
[60] Provisional application No. 60/039,251, Feb. 25, 1997.

[51] Int. Cl.$^7$ ........................................................ A61F 5/48
[52] U.S. Cl. .................................. 128/885; 128/DIG. 25; 600/29
[58] Field of Search ..................... 128/885, 886, 128/DIG. 25; 600/29–31

[56] References Cited

U.S. PATENT DOCUMENTS

| | | | |
|---|---|---|---|
| 2,564,399 | 8/1951 | Fanken | 128/283 |
| 3,347,226 | 10/1967 | Harrower | 128/850 |
| 3,642,004 | 2/1972 | Osthagen et al. | 128/349 |
| 3,731,670 | 5/1973 | Loe | 128/1 |
| 3,812,841 | 5/1974 | Isaacson | 128/1 R |
| 3,924,631 | 12/1975 | Mancusi, Jr. | 128/346 |
| 3,926,175 | 12/1975 | Allen et al. | 128/1 |
| 4,306,705 | 12/1981 | Svensson | 251/149.9 |
| 4,555,242 | 11/1985 | Saudagar | 604/96 |
| 4,679,546 | 7/1987 | van Waalwijk van Doorn et al. | 128/1 |
| 4,800,900 | 1/1989 | French | 128/885 |
| 4,804,375 | 2/1989 | Robertson | 604/323 |
| 4,909,785 | 3/1990 | Burton et al. | 604/54 |
| 4,994,020 | 2/1991 | Polyak | 600/31 |
| 5,004,454 | 4/1991 | Beyar et al. | 600/30 |
| 5,014,757 | 5/1991 | Donaldson et al. | 141/114 |
| 5,030,199 | 7/1991 | Barwick et al. | 600/29 |
| 5,041,092 | 8/1991 | Barwick | 604/104 |
| 5,112,306 | 5/1992 | Burton et al. | 604/101 |
| 5,114,398 | 5/1992 | Trick et al. | 600/29 |
| 5,140,999 | 8/1992 | Ardito | 128/885 |
| 5,188,120 | 2/1993 | White et al. | 128/778 |
| 5,234,409 | 8/1993 | Goldberg et al | 604/96 |
| 5,509,889 | 4/1996 | Kalb et al. | 600/30 |
| 5,513,660 | 5/1996 | Simon et al. | 128/885 |

FOREIGN PATENT DOCUMENTS

| | | |
|---|---|---|
| 0 407 218 A 1 | 1/1991 | European Pat. Off. . |
| 0 407 218 A1 | 1/1991 | European Pat. Off. . |
| 1616477 | 7/1967 | Germany . |
| 41 35 502 C 1 | 2/1993 | Germany . |
| 413 5502 C1 | 5/1993 | Germany . |
| 4137 751 A1 | 5/1993 | Germany . |
| 2 235 383 | 3/1991 | United Kingdom . |
| 95/17143 | 6/1995 | WIPO . |
| 96/03942 | 2/1996 | WIPO . |
| 98/22039 | 5/1998 | WIPO . |

*Primary Examiner*—Michael A. Brown
*Attorney, Agent, or Firm*—Hamilton, Brook, Smith & Reynolds, P.C.

[57] ABSTRACT

An involuntary urine control device (IUCD) having an inflatable collar membrane. The IUCD is inserted a short distance into the distal end of the urethra of a subject user. The IUCD includes the collar membrane which comprises an open ended tube of inflatable membrane material, typically about 30% to 90% of the length of the device. The collar membrane, in its inflated state, serves the purpose of providing sealing between the periphery of the urine control device and the urethra wall. The collar membrane is inflated to move radially outward once the urine control device is inserted into the distal end of the urethra of a patient by the external supply of a fluid. The collar membrane in its deflated state, namely with the inflating fluid removed, is substantially flush with the external diameters of the outer jacket of the urine control device to accommodate the thickness of the collar membrane.

23 Claims, 6 Drawing Sheets

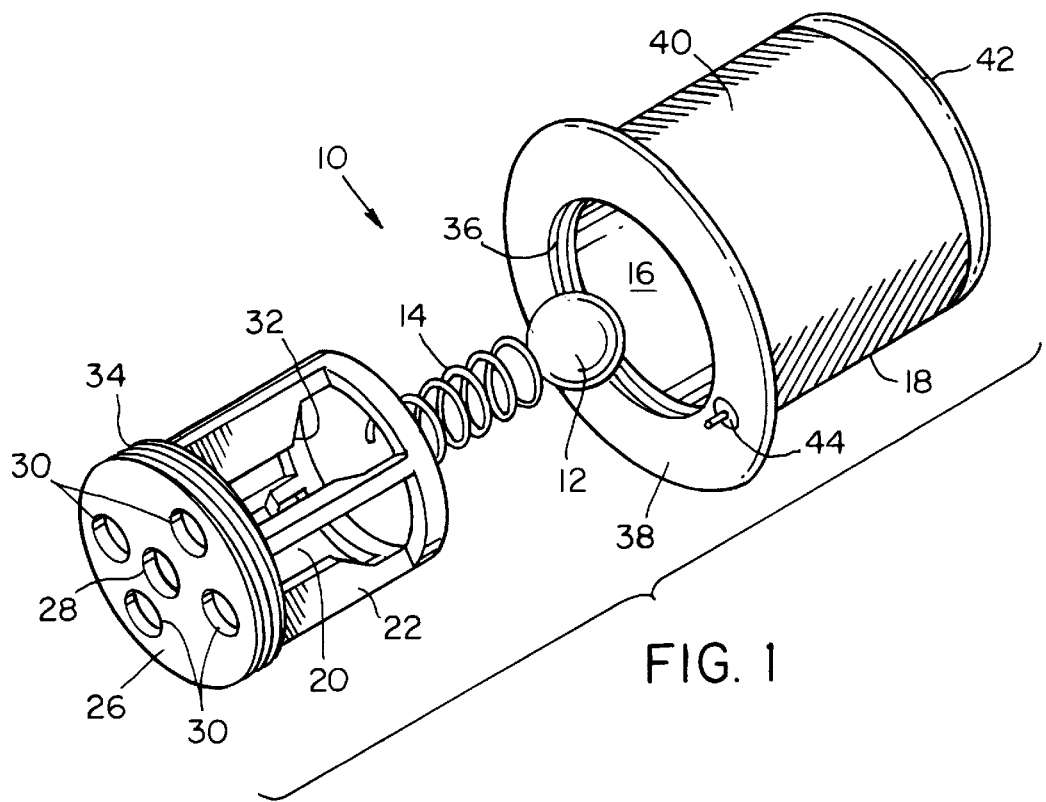
FIG. 1
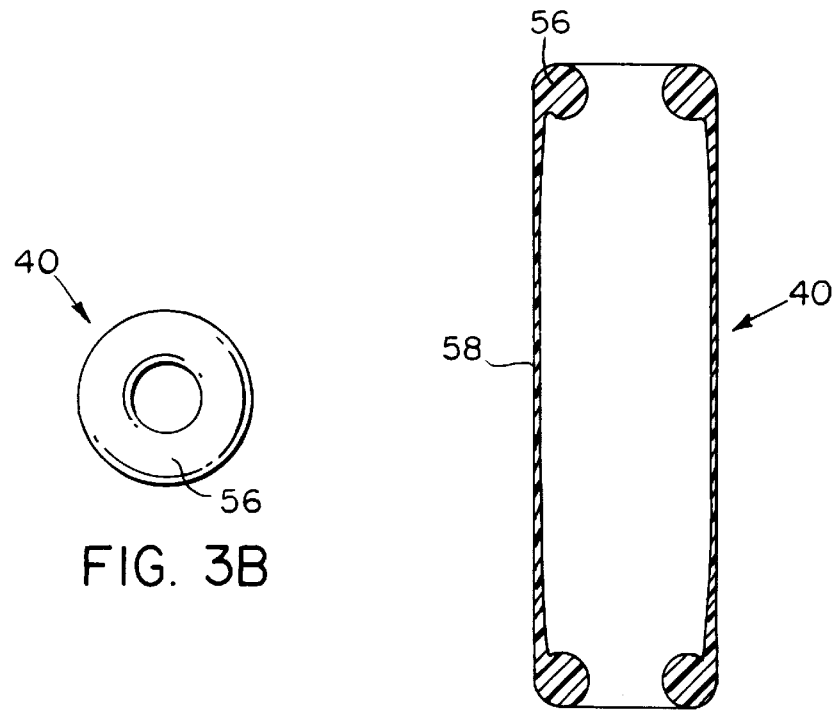
FIG. 3B
FIG. 3A

URINE CONTROL DEVICE

RELATED APPLICATIONS

This application claims benefit to U.S. Provisional Application No. 60/039,251 filed on Feb. 25, 1997 and this application is a Continuation-In-Part of U.S. patent application Ser. No. 08/979,099, filed Nov. 26, 1997, which is a continuation of U.S. patent application Ser. No. 08/731,246 filed Oct. 11, 1996, which is a divisional of U.S. patent application Ser. No. 08/333,860 filed Nov. 3, 1994, all of which are hereby incorporated by reference.

BACKGROUND OF THE INVENTION

There are a wide variety of structures and devices designed for the valving of bodily fluid, such as urine, and particularly to valve control devices for persons suffering from urinary incontinence. Urinary incontinence is a particularly long-recognized medical problem and relates to the inability of a subject to voluntary control the elimination and function of the bladder, which can result from numerous causes.

SUMMARY OF THE INVENTION

The invention relates to an involuntary urine control device (IUCD) having an inflatable collar membrane. The IUCD is inserted a short distance into the distal end of the urethra of a subject user. The IUCD includes the collar membrane which comprises an open-ended tube of inflatable membrane material, typically about 30% to 90% of the length of the device, and having an outer diameter of 0.2 to 0.35 inch, and with thickened sealing O-rings at each open end of the collar membrane. The inflatable membrane member is generally "olive" or "football" shaped for the male urethra, and has multiple convolutions for the female urethra.

The collar membrane, in its inflated state, serves the purpose of providing sealing between the peripheral of the urine control device and the urethra wall, as well as preventing the urine control device from migrating or sliding outward from its inserted position by the hydraulic pressure of the urine and, possibly, the transient involuntary forces of coughing and sneezing. The collar membrane is inflated to move radially outward once the urine control device is inserted into the distal end of the urethra of a patient by the external supply of a fluid via a hand pump or a syringe functioning as a fluid transfer device. The inflating fluid can be air, water, saline solution or any such natural or synthetic fluid, that is not harmful to the urinary tract of a human. The collar membrane in its deflated state, namely with the inflating fluid removed, is substantially flush with the external diameters of the outer jacket of the urine control device to accommodate the thickness of the collar membrane.

The collar membrane is constructed in a preferred embodiment of a flexible bio-compatible polymer which possesses the suitable properties of flexibility for repeated operations of inflation and deflation, and sufficiently low permeability with respect to the fluid used to inflate the collar membrane. The collar membrane has a tubular overall configuration with two open ends.

In order to prevent migration of the urine control device outwardly from the patient's urethra, a suitable amount of frictional force must exist between the urethral wall and the device. It is, however, desirable to minimize the application of force in order to avoid potential irritation to the mucosa of the urethra. The current invention also deals with the approach to minimize the force exerted on the urethra wall by way of distributing the force more evenly over a larger contact area between the inflated collar membrane and the urethral wall. Given the difference between the anatomies of males and females, the collar membrane of the urine control devices are configured differently.

While the above applies to the invention in general, specific embodiments can be tailored to specific uses. The portion of the male urethra channel where the urine control device situates, namely, within approximately one inch from the male external urethra orifice, is named fossa navicularis which retains a natural configuration of, an olive, or a miniature American football. In order to allow a maximum contact surface area between the collar membrane and the fossa navicularis, it is desirable that the collar membrane in its inflated state achieve this "olive" configuration. This intention also deals with the construction of the collar membrane to positively achieve this "olive" configuration in its inflated state for the male urine control device by way of using a thin walled membrane tube with a longitudinally tapered wall thickness. The wall thickness of the membrane tube is thicker at the two ends, and thinner in the middle portion. When inflated, the center portion of the collar membrane will bulge out more substantially than the ends under the same inflating pressure exerted by the inflating fluid, thus allowing the collar membrane to form the approximate shape of an "olive", rather than an elliptical configuration of an ordinary flexible membrane with an uniform wall thickness.

In addition to an embodiment for use in the male urethra, an embodiment can be tailored for use in the female urethra. The portion of the female urethra channel where the urine control device situates, namely approximately one inch within the female external urethra orifice, in contrast with the male fossa navicularis, is substantially tubular with a reasonably uniform inner diameter. In order to provide a maximum contact surface between the urine control device and the distal end of the female urethra, it is desirable that the collar membrane contacts the urethra wall at more than one location such that the total frictional force required to provide sealing against the urinary hydraulic pressure and other transient involuntary forces is distributed.

The inflatable collar membrane to distribute the sealing force for the female urine control device has a thin walled membrane tube with multiple convolutions of tapered wall thickness. Within each convolution, the wall thickness of the membrane tubular section is thicker at two ends and thinner in the middle. The entire membrane tube is constructed with two to four such convolutions of tapered wall sections. The two ends of the collar membrane are similar to the inflatable collar membrane for use in the urethra of male with a pair of sealing rings.

When inflated, the thinner wall portions of the collar membrane will bulge out more substantially than the thicker-walled portions under the same inflating pressure exerted by the inflating fluid, thus forming multiple sealing contacts in a sinusoidal wave fashion, between the collar membrane of the female urine control device and the female urethra wall. The multiplicity of the contact points would naturally correspond to the number of convolutions of tapered wall sections.

The thickness of the membrane for both embodiments of the male urine control device and the female urine control device, dictated by the choice of the membrane material and the frictional force required to achieve the prevention of outward mobility of the urine control device, can vary from several thousandths of an inch at the thinner portion of the membrane tube to approximately 0.01 to 0.03 at the sealing ring ends of the membrane.

To further enhance the functionality of the collar membrane, the outer surface of the collar membrane may be formed with a textured pattern. This textured pattern impacts additional friction force for retaining the urine control device in the uretha, and allows the capturing within the textured structure of a lubricating ointment which may be used to reduce the sensation of inserting the urine control device into the urethra. The said ointment retained in the textured structure will also enhance sealing between the urine control device and the urethral wall to prevent urine leakage.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 1 is an exploded perspective view of the urine control valve of the invention;

FIG. 3A is a cross sectional view of a collar membrane;

FIG. 3B is a front view of the collar membrane;

DESCRIPTION OF THE EMBODIMENTS

Figure 2:
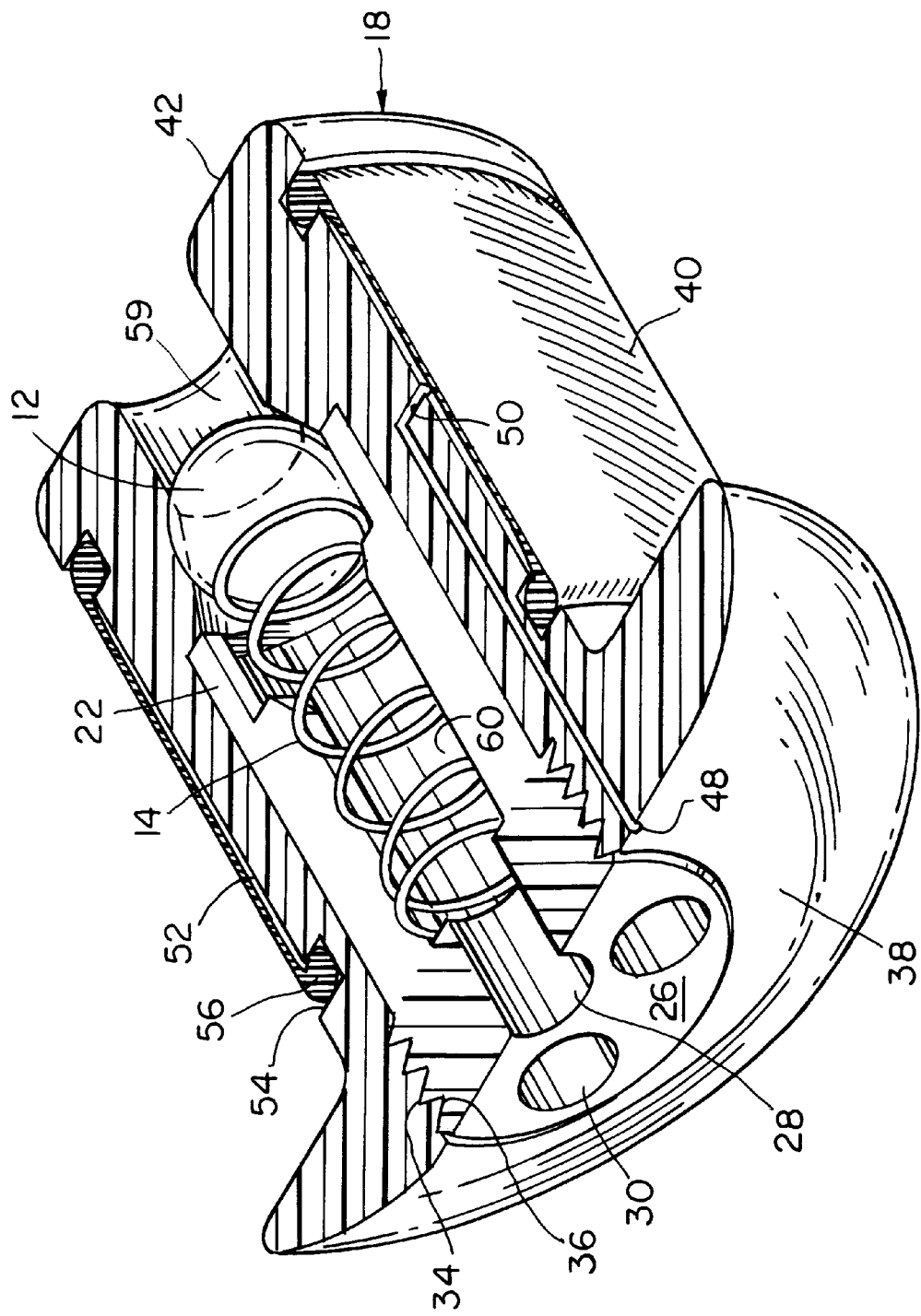
FIG. 2 is a partial sectional, perspective view of the urine control valve of FIG. 1.

Referring to the drawings in detail, where like numerals indicate like elements, there is illustrated an involuntary urine control apparatus in accordance with the present invention designated generally as 10.

As illustrated, FIG. 1 shows the involuntary urine control apparatus 10 in an exploded perspective view, with the Teflon-coated metal ball 12 positioned to rest on one end of the tension-biased spring 14 extending within a valve chamber 16 of a valve jacket 18. The other end of the spring 14 rests in a central discharge passageway 20 within the four spaced-apart, inwardly extending spring guide fingers 22 on a jacket head 26. The spring guide fingers 22 extend inwardly into the valve chamber 16 of the valve jacket 18.

The jacket head 26 has a central discharge outlet 28 and four surrounding, spaced-apart discharge outlets 30. The surrounding discharge outlets 30 are each interposed between the spring guide fingers 22. The four inwardly extending spring guide fingers 22 each have a portion cut out thereon on their inner surface to provide a ball valve stop area 32 for the Teflon-coated metal ball 12. The jacket head 26 has a threadable, screw-type fastener 34 on its outer perimeter which is received by a threaded opening 36 on the inner perimeter of the end of the valve jacket 18.

The valve jacket 18 has an outwardly, radially extending flange 38 on its outer distal end for retaining the apparatus 10 in a position outside and against the urethral opening of the subject. The involuntary urine control device 10 has an inflatable collar membrane 40, as referred to as a jacket membrane collar, that overlies a portion of the elongated cylinder-type valve jacket 18. A rounded end surface 42 is provided on the urine control device 10 to provide a comfortable fit for the subject within the urethra. A fluid pump valve 44 is shown on the outer surface of the flange 38 to provide for inflation of the inflatable collar membrane 40 after the apparatus 10 is inserted within the urethra to secure and stabilize the apparatus against the urethral wall, as described below.

FIG. 2 is a cutaway perspective sectional view of the assembled involuntary urine control apparatus 10 with the Teflon-coated metal ball 12 resting on the tension-biased spring 14 within the spring guide fingers 22 on the jacket head 26. The drawing further depicts the head 26 and jacket 18 threaded areas 34 and 32 for the threadable, removable securing of the jacket head 26 to the valve jacket 18. The central discharge passageway outlet 28 and two of the spaced apart discharge chamber outlets 30 are shown.

The outer flange 38 of the apparatus 10 has an opening 48 for a valve capillary tube passageway 50 leading to an inflatable collar membrane chamber 52. The inflatable collar membrane chamber 50 is a slightly narrower band on the valve jacket 18 having a slightly narrower outer diameter than the remainder of the valve jacket 18. The inflatable collar membrane chamber 52 is surrounded by the inflatable collar membrane 40 and narrowed by the thickness of the inflatable collar membrane 40 in a deflated position, as shown in FIG. 2, such that the inflatable collar membrane 40 is flush with the rest of the valve jacket 18. The collar membrane 40 has a length of typically about 30% to 90% of the length of the device 10. The valve jacket 18 is illustrated with the rounded end 42 and the urethral discharge passageway inlet 59 to a chamber passageway 60.

FIGS. 3A and 3B illustrate the cross sectional view and end view of the inflatable collar membrane 40 prior to installation. The inflatable collar membrane 40 is cylindrical in shape and has sealing rings 56 at each end to be received in grooves 54 in the outer circumference of the valve jacket 18 as seen in FIG. 2. In a preferred embodiment, the sealing rings 56 are O-rings in shape. In one of the preferred embodiments, the sealing rings 56 are formed of the same material as the rest of the inflatable collar membrane 40.

Figure 4:
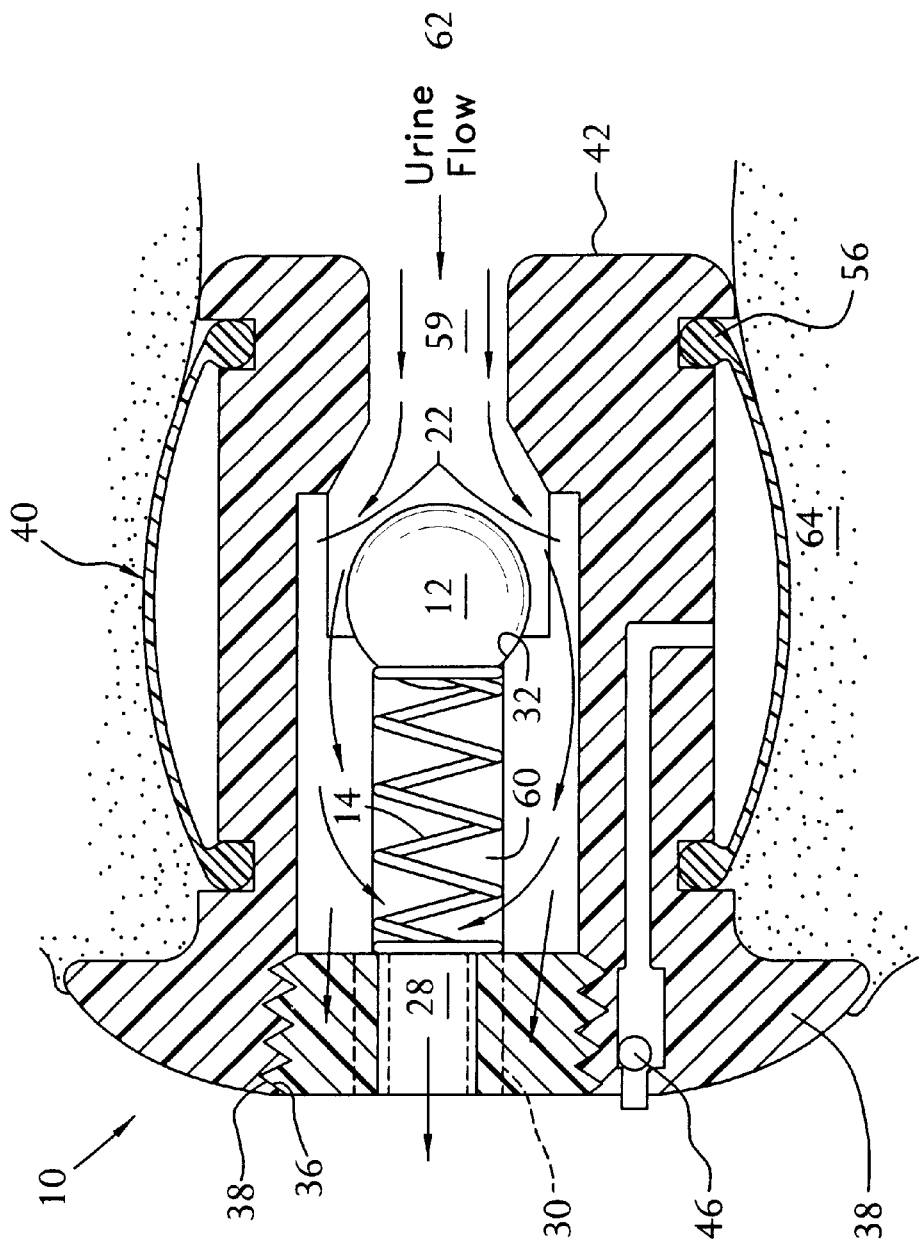
FIG. 4 is a sectional view of the urine control valve of FIG. 2 with the ball valve in the urine flow position.
Figure 5:
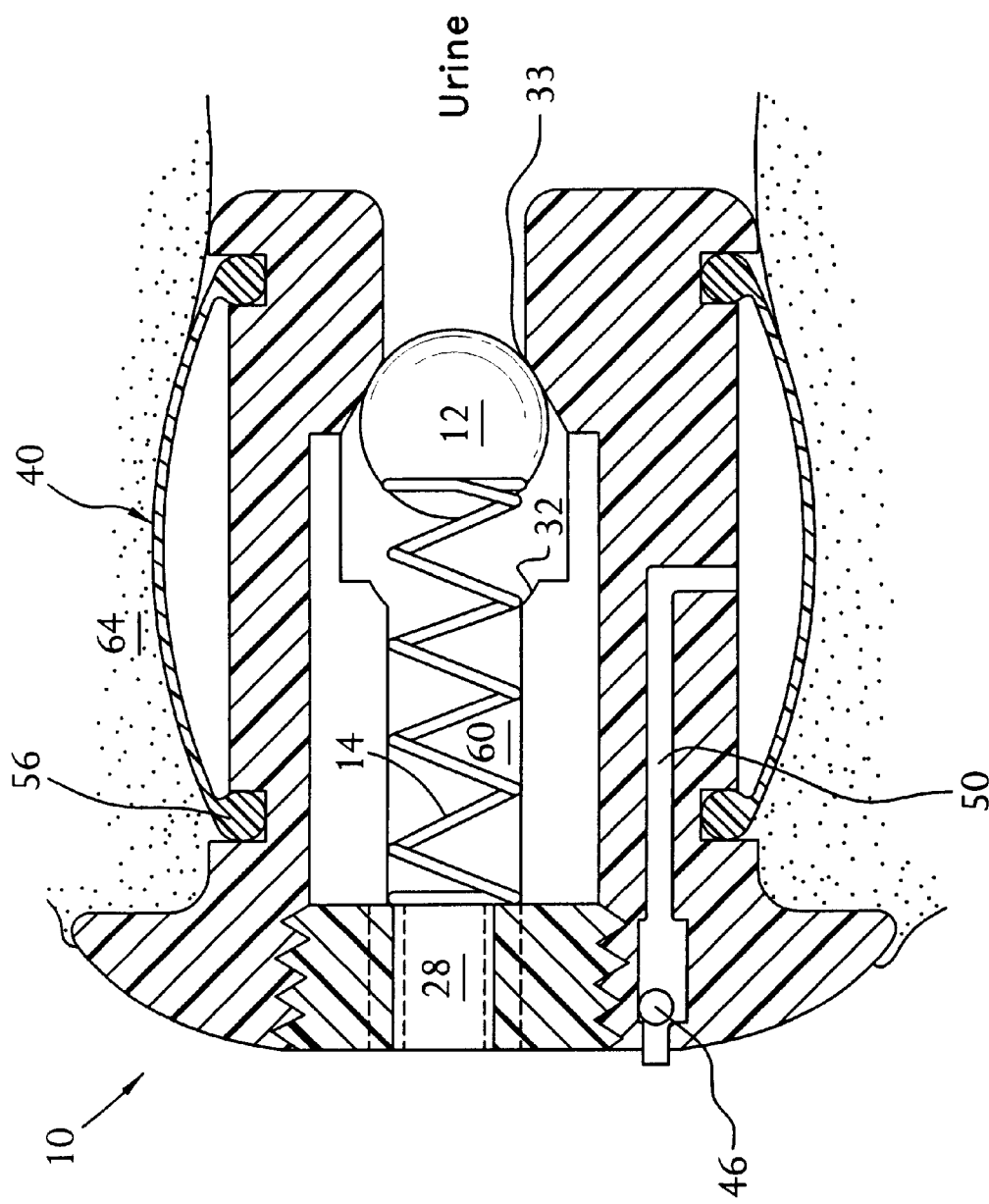
FIG. 5 is a sectional view of the ball valve of FIG. 2 with the ball valve in the urine stop position.

The inflatable collar membrane 40 is a thin walled membrane tube 58. The inflatable collar membrane 40 has a longitudinal axis. The longitudinal axis is not necessarily, and in a preferred embodiment is not, the same longitudinal axis as that for the chamber passageway, since the jacket head 26 is off-set from the center of the jacket 18 to allow for the valve capillary tube passage 50 as best seen in FIGS. 4 and 5. The inflatable collar membrane 40 narrows in thickness as it moves away from the sealing rings 56 and toward a center point between the sealing rings 56. The thickness is symmetric about the longitudinal axis and the center point. The inflatable collar membrane 40 shown in FIGS. 1–5 is for use in a urethra of a male and has one convolution of the tapered section.

In another preferred embodiment, the two ends of the collar membrane are constructed with sealing rings 56 shaped like an "O-ring" which are made of a different elastomeric material. The sealing rings 56 serve the purpose of providing the collar membrane 40 a fixed position on the external surface of the urine control device 10, and as a positive sealing mechanism to prevent or minimize the loss of inflation fluid captured within the inflated collar membrane 40.

The position fixing function is further enhanced with the provision of the pair of grooves 54 which have a width and a depth substantially similar to the diameter of the sealing rings 56. In a preferred embodiment, the sealing rings 56 are approximately 0.01 to 0.03 inch in thickness. These grooves 54 can either be substantially square, rectangular, or circular in cross-sectional area. The inner diameter of the sealing rings 56 are to be slightly smaller than the outer diameter of the depth of the groove 54 in the urine control device 10. The sealing rings 56 are installed by either mechanically stretching radially outward, or heat-shrunk for placement onto the urine control device 10 when the urine control device is assembled.

After the placement, the compression strength of the sealing rings 56 will serve the purpose of sealing the fluid inside the inflated collar membrane 40. It is also possible to apply other methods such as using an adhesive, or plastic welding techniques, or using a clip-like compression mechanical device, made from either metallic or non-metallic materials, to further enhance the sealing of the fluid within the collar membrane 40, and more securely affixing the collar membrane onto the urine control device 10. The sealing rings 56 are incorporated into the collar membrane by either casting-in-place with the body, the thin walled membrane tube 58, of the membrane collar 40 or by joining the separately fabricated sealing rings 56 with the remaining portion of the collar membrane 40.

FIG. 4 is an enlarged, side sectional view of the involuntary urine control apparatus of the invention in the open, urine flow position, with the polymer-coated metal ball 12 resting against the ball valve stop 32 created by the inwardly extending spring guide fingers 22. The ball 12 is held in this position by means of a magnet, employed by the subject, being placed in proximity to the involuntary urine control apparatus 10, permitting the magnetic field of the magnet means to activate the magnetically-activated ball valve means and moving the ball 12 away from the ball valve seat 33 to the open position as desired.

The urine flow 62 is now able to enter the central discharge passageway 20 and flow out of the control valve 10 through the central discharge passageway outlet 28 and the surrounding, spaced apart discharge outlets 30 located in the jacket head 26. The jacket head 26 is secured to the valve jacket 18 by the threadable screw-type fastener 34 threaded to the threaded opening 36 on the valve jacket 18.

The inflatable collar membrane 40 is shown in its inflated condition. The inflatable collar membrane 40 has generally an elliptical, or olive or football shape. The inflatable collar membrane 40 is inflated by air entering the pump 44 and passing through the valve capillary tube passageway 50, The inflatable collar membrane 40 rests in a secure manner against the urethral wall 64.

The portion of the male urethra channel where the urine control device 10 is situated, namely within approximately one inch from the male external urethra orifice, is named fossa navicularis which retains a natural configuration of an olive, or a miniature American football. In order to allow a maximum contact surface area between the collar membrane and the fossa navicularis, the collar membrane 40 in its inflated state has a similar "olive" configuration.

Referring to FIGS. 3A, 3B, and 4, the collar membrane 40 is constructed to positively achieve this "olive" configuration in its inflated state for the male urine control device by way of using a thin walled membrane tube 58 with a longitudinally tapered wall thickness. The wall thickness of the membrane tube is thicker at the two ends, where the sealing rings 56 are embedded, and thinner in the middle portion of the tube. When inflated, the center portion of the collar membrane will bulge out more substantially than the ends under the same inflating exerted by the inflating fluid, thus allowing the collar membrane to form the approximate shape of an "olive", rather than a configuration of an ordinary flexible membrane with an uniform wall thickness.

The outer flange 38 retains the apparatus 10 in a secure manner against the subject's urethral opening, and at the other end the rounded end 42 of the valve jacket 18 provides for comfortable insertion and withdrawal of the apparatus 10 within the urethra. The inflatable collar membrane 40 can also be deflated by means of inserting a rod or pin into the pump valve 44, and dislodging a check ball 46 within the valve to allow fluid to escape the valve pump 44.

FIG. 5 is an enlarged, side sectional view of the involuntary urine control apparatus of the invention 10 in a closed, non-urine flow position, with the Teflon-coated metal ball 12 resting against the ball valve seat 19 of the jacket 18. The metal ball 12 biased by the tension-biased spring 14, which at the other end is resting against the jacket head 26 within the spring guide fingers 22. The inflatable collar membrane 40 is shown in its inflated condition resting in a secure manner against the urethral wall 64. Urine flow 62 is prevented from entering the discharge chamber passageway 34 and out the discharge passageway outlets 28 and 30 by the tension-biased metal ball 12 held tensionally against the ball valve seat 33. The outer flange 38 retains the apparatus 10 in a secure manner against the subject's urethral opening.

Figure 6:
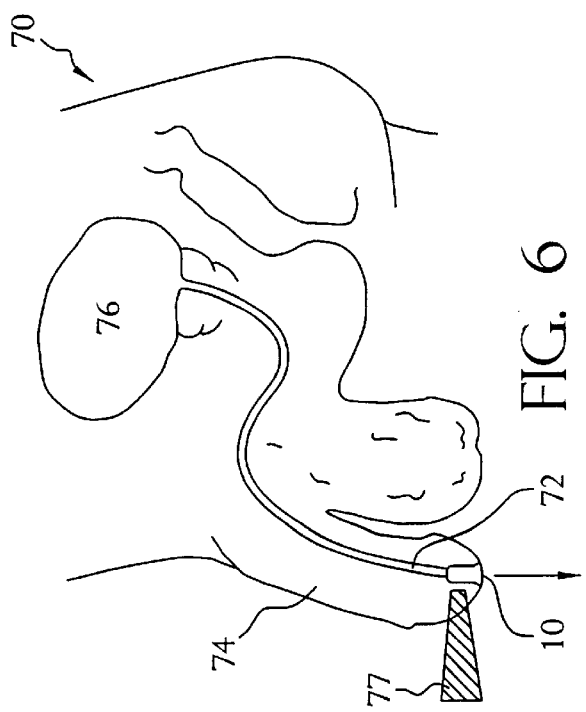
FIG. 6 is a schematic illustration of the urine control valve in use.

FIG. 6 is a schematic view of the involuntary urine control device 10 in use in a subject 70, here illustrated as a male subject. The apparatus is within the urethra 72 at the end of the penis 74 with the bladder 76 being emptied by means of the magnet 78 placed in a proximal manner to the apparatus 10, opening the valve to allow for urine flow 62 out of the penis 74.

Figure 7:
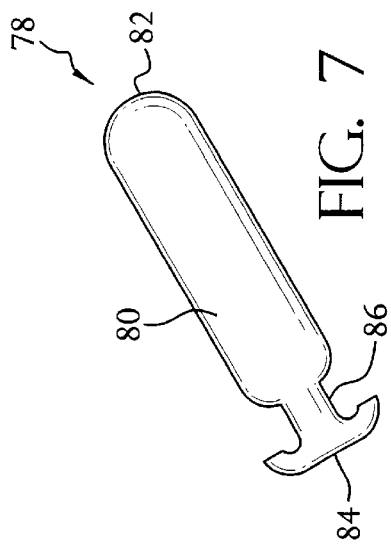
FIG. 7 is a side elevational view of one of the dowels of the urethra tool measuring kit of the invention.

FIG. 7 is a side elevational view of a measuring dowel tool 78, having a cylindrical shape with a tool body 80 having smooth, rounded sides and a smooth, rounded end 82 to provide for comfort of the subject when inserting and withdrawing the measuring dowel, and a flange element 84 at the outer end for grasping by the user while inserting or withdrawing the measuring tool from the urethra. The flange element 84 is connected to the tool body 80 by means of a neck 86 of lesser diameter than the tool body. The measuring kit, including the measuring dowel tool 78, has a plurality of measuring dowel tools with the body 80 having different, selected diameters to allow for measuring the urethra to provide for the proper fit of the apparatus within the subject during use. Below is a diagram of the various diameters of the 18 dowels as typically included in the measuring kit:

| Number | Diameter |
|--------|----------|
| 1  | .250 |
| 2  | .255 |
| 3  | .260 |
| 4  | .265 |
| 5  | .270 |
| 6  | .275 |
| 7  | .280 |
| 8  | .285 |
| 9  | .290 |
| 10 | .295 |
| 11 | .300 |
| 12 | .305 |
| 13 | .310 |
| 14 | .315 |
| 15 | .320 |
| 16 | .325 |
| 17 | .330 |
| 18 | .335 |

In operation, the involuntary urine control apparatus of the invention comprises an outer valve jacket 18 comprising a radially outwardly-extending flange 38 at one end, a smooth rounded outwardly-curved end 42 at the other end, this end having an urine discharge passageway inlet 59 in the middle thereof for the entry of urine to be discharged, and an elongated, cylindrical valve jacket 18 between the inlet and outlet to contain the metal ball 12, tension-biased spring 14 and spring guide fingers 22 of the apparatus 10.

The valve jacket 18 has the inflatable collar membrane 40 extending in a slightly diameter-enlarged manner to provide for securing and stabilizing the apparatus 10 inside the urethra against the urethral walls 64 when the collar 40 is inflated. The inflatable collar membrane 40 may be inflated by means of a valve pump 44 pumping fluid, such as a gas or liquid, into the valve capillary tube passageway 50. The outer flange 38 provides for the retaining of the apparatus against the outside of the subject's urethral opening, preventing the apparatus 10 from sliding within the urethra, and the smooth, curved inner end 42 is shaped, thus to provide for comfort of the subject during insertion, withdrawal and use.

After the apparatus 10 is inserted and secured within the subject's urethra, the Teflon-coated metal ball 12 rests in a tension-biased condition against the ball valve seat 33 preventing the flow of urine into the discharge chamber passageway 60. When desired by the subject, a magnet is held adjacent to the apparatus from the outside of the subject's body, to move the ball downwardly against the spring until it rests against the ball valve stop 23 inside the spring guide fingers 22 within the valve jacket 18. In this open position, the urine flow proceeds through the discharge chamber passageway 60, the central 28 and surrounding 30 discharge passageway outlets and out of the jacket head 26. When the bladder is emptied, the subject simply moves the magnet away from the apparatus and the ball 12 is released from the magnetic force and returned to its stop position against the ball valve seat 33, preventing any further urine flow.

It should be noted that if there is sufficient pressure from the urine stored in the bladder exerted on the magnetic ball 12, the ball will move down to allow for the flow of the urine to prevent harmful backup of urine within the urethra. Further the inflatable collar membrane 40, being snug-fit against the urethral wall, prevents any leakage from the bladder between the valve apparatus and the urethral wall.

The inflatable collar membrane 40 in the previous embodiment is designed for use in the urethra of a male, which has an "olive" shape. The portion of the female urethra channel where the urine control device situates, namely approximately one inch within the female external urethra orifice, in contrast with the male fossa navicularis, is substantially tubular with a reasonably uniform inner diameter. In order to provide a maximum contact surface between the urine control device 10 and the distal end of the female urethra, an inflatable collar membrane contacts the urethra wall at more than one location such that the total frictional force required to provide sealing against the urinary hydraulic pressure and other transient involuntary forces is distributed.

Figure 8B:
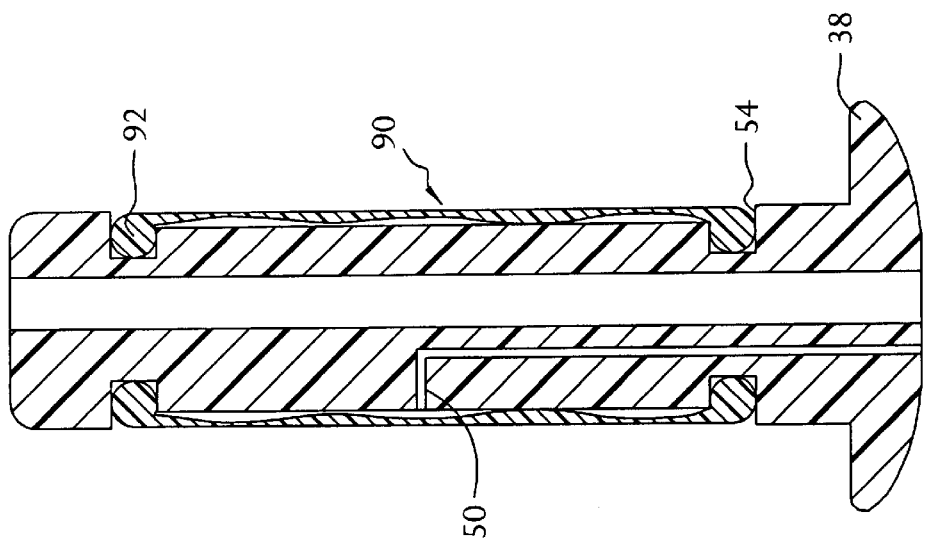
FIG. 8B is a schematic illustration of the collar membrane for a female on the urine control device in a deflated position.
Figure 8A:
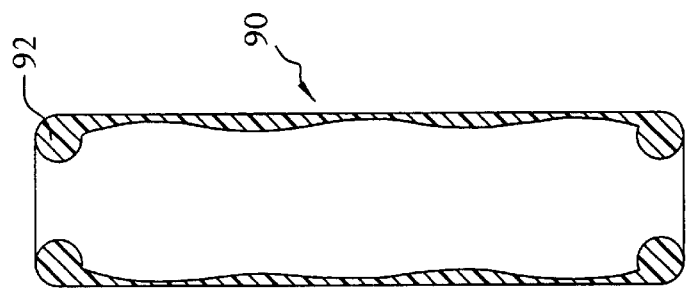
FIG. 8A is a cross sectional view of a collar membrane for use in a urethra of a female.

FIG. 8A illustrates the unassembled inflatable collar membrane 90 for use in a urethra of a female. The urethra of a female has a female IUCD, showing sealing rings 92 positioned at either end. As in the first embodiment, in a preferred embodiment, the sealing rings 92 are O-rings.

FIG. 8B illustrates the inflatable collar membrane 90 installed on the valve jacket 18 of the involuntary urine control device 10. The inflatable collar membrane 90 is shown in an uninflated position.

Figure 8C:
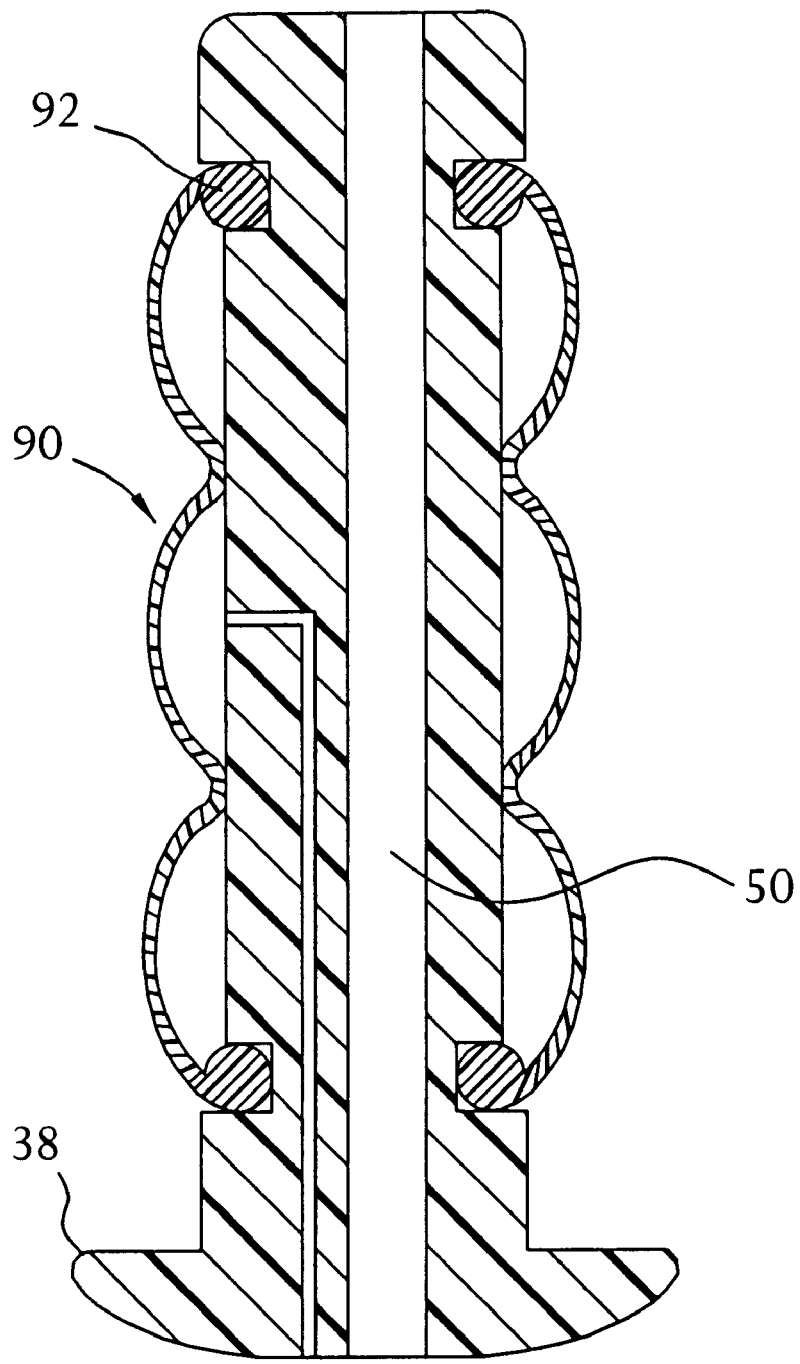
FIG. 8C is a schematic illustration of the collar membrane for a female on the urine control device in an inflated position.

FIG. 8C illustrates the involuntary urine control device 10 with the inflatable collar membrane 90 for use in a urethra of a female in an inflated position.

While the collar membrane is described in particular for use with the IUCD apparatus and method of the parent application, it is recognized that the collar membrane may be usefully employed with other urethra insertable urine control devices or useful in other devices for insertion and removal in a restricted body cavity.

The collar membrane, in its inflated state, serves the purpose of providing sealing between the peripheral of the urine control device and the urethra wall, as well as preventing the urine control device from migrating or sliding outward from its inserted position by the hydraulic pressure of the urine and, possibly, the transient involuntary forces of coughing and sneezing. The collar membrane is inflated to move radially outward once the urine control device is inserted into the distal end of the urethra of a patient by the external supply of a fluid via a hand pump or a syringe functioning as a fluid, that is not harmful to the urinary tract of a human. The collar membrane in its deflated state, namely with the inflating fluid removed, is substantially flush with the external diameters of the outer jacket of the urine control device to accommodate the thickness of the collar membrane.

The collar membrane is constructed of a flexible biocompatible polymer which possesses the suitable properties of flexibility for repeated operations of inflation and deflation, and sufficiently low permeability with respect to the fluid used to inflate the collar membrane. Examples of this desirable material for the collar membrane could include, but are not limited to, silicone, natural latex, synthetic latex, or other natural or synthetic polymeric materials in their substantially pure states, or composites by blending, coating or laminating with one another. The collar membrane has a tubular overall configuration with two open ends. The length of tube will cover a substantial portion (no more than 90%, but no less than 30%) of the length of the urine control device. The outer diameter of the membrane tube can range from approximately 0.20 inch to approximately 0.35 inch.

EQUIVALENTS

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

What is claimed is:

1. An inflatable collar for a urethra insertion device, the collar comprising:
    a cylindrical tube having a first end and a second end, the cylindrical tube being formed of an inflatable material wherein the thickness of the material of the cylindrical tube varies by at least 50 percent; and
    a sealing element at each end of the cylindrical tube that seals the tube to the insertion device.

2. The inflatable collar of claim 1 wherein the material of the cylindrical tube narrows in thickness between the sealing element from one end of the cylindrical tube to the other end of the cylindrical tube.

3. The inflatable collar of claim 1 wherein the material of the cylindrical tube has at least two areas with reduced thickness between the sealing element at each end of the cylindrical tube.

4. The inflatable collar of claim 1 wherein the sealing element is an O-ring adapted to be received in a groove in the insertion device.

5. The inflatable collar of claim 4 wherein the inner diameter of the O-rings is smaller than the inner diameter of the groove.

6. An urine control valve apparatus comprising
    a cylindrical jacket having an outlet end and an inlet end;
    the cylindrical jacket having a pair of grooves around the outer diameter;
    an inflatable collar membrane having a cylindrical tube having a pair of open ends and a sealing ring at each end of the cylindrical tube for securing within the grooves on the outer diameter of the cylindrical jacket, the cylindrical tube formed of an inflatable material of varying thickness.

7. The urine control valve apparatus of claim 6 wherein the cylindrical jacket has a smaller diameter between the grooves by the thickness of the inflatable collar such that the inflatable collar when in a deflated position is flush with the cylindrical jacket.

8. The urine control valve apparatus of claim 7 further comprising a radially extended flange having an external surface from the one end of the jacket adapted to fit about and adjacent the open distal end of the urethra.

9. The urine control valve apparatus of claim 6 further comprising a passageway between the inlet end and the outlet end and a valve in the passageway for limiting the flow through the passageway.

10. The urine control valve apparatus of claim 9 wherein the valve comprises a ball moveable between two positions and biased by a spring to a closed position.

11. The urine control valve apparatus of claim 9 further comprising a finger operated pump to be employed by a subject to inflate the collar membrane and to stabilize the jacket in position within the urethra.

12. The urine control valve apparatus of claim 6 wherein the cylindrical tube of the collar having varying thickness.

13. The urine control valve apparatus of claim 12 wherein the cylindrical tube of the collar narrows in thickness as it moves from the sealing rings.

14. The urine control valve apparatus of claim 13 wherein the thickness of the inflatable collar membrane varies from greater than 0.01 inches at the sealing rings to less than 0.002 inches at the midpoint between the sealing rings.

15. The urine control valve apparatus of claim 12 wherein the material of the cylindrical tube has at least two areas with reduced thickness between the sealing rings.

16. The urine control valve apparatus of claim 6 wherein the inflatable collar membrane extends over between 30 and 90 percent of the cylindrical jacket.

17. The urine control valve apparatus of claim 6 wherein the sealing ring is an O-ring and the inner diameter of the O-rings is smaller than the inner diameter of the groove.

18. A method of positioning an urine control device in a urethra comprising the following steps:
    providing the urine control device having a cylindrical jacket having an outlet end and an inlet end, the cylindrical jacket having a pair of grooves around the outer diameter and an inflatable collar membrane having a cylindrical tube having a pair of open ends and a sealing ring at each end of the cylindrical tube for securing within the grooves on the outer diameter of the cylindrical jacket, the cylindrical tube formed of an inflatable material of varying thickness;
    slideably inserting the urine control device into the open distal end of the urethra;
    positioning a flange of the urine control device adjacent to the open distal end of the urethra; and
    inflating the inflatable collar membrane to retain the urine control device in the urethra.

19. The method of claim 18 wherein the urethra has a cylindrical shape and the inflatable collar membrane has a plurality of sinusoidal waves.

20. The method of claim 18 wherein the urethra has an olive shape and the inflatable collar membrane has a complementary shape.

21. The method of claim 18 further comprising the step of deflating the inflatable collar membrane for removal of the urine control device from the urethra.

22. The method of claim 18 wherein the inflating step is done with a hand operated pump.

23. The method of claim 18 further comprising the step of tailoring the thickness of the inflatable collar membrane such that upon inflation the collar membrane complements the shape of the urethra.

* * * * *